US012569212B2

(12) United States Patent
Ogasawara et al.

(10) Patent No.: US 12,569,212 B2
(45) Date of Patent: Mar. 10, 2026

(54) MEDICAL IMAGE PROCESSING APPARATUS, X-RAY DIAGNOSTIC APPARATUS, AND MEDICAL IMAGE PROCESSING METHOD

(71) Applicant: CANON MEDICAL SYSTEMS CORPORATION, Otawara (JP)

(72) Inventors: Jumpei Ogasawara, Nasushiobara (JP); Hajime Yoshida, Nasushiobara (JP); Yasuto Hayatsu, Otawara (JP); Kunio Shiraishi, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 273 days.

(21) Appl. No.: 18/459,491

(22) Filed: Sep. 1, 2023

(65) Prior Publication Data

US 2024/0081770 A1 Mar. 14, 2024

(30) Foreign Application Priority Data

Sep. 9, 2022 (JP) ................................. 2022-143654

(51) Int. Cl.
*A61B 6/00* (2024.01)
*A61B 6/03* (2006.01)
(Continued)

(52) U.S. Cl.
CPC ............ *A61B 6/5258* (2013.01); *A61B 6/032* (2013.01); *A61B 6/4085* (2013.01); *G06T 5/70* (2024.01);
(Continued)

(58) Field of Classification Search
CPC ....... A61B 6/032; A61B 6/5258; A61B 6/461; A61B 6/5205; A61B 6/4233; A61B 6/542;
(Continued)

(56) References Cited

U.S. PATENT DOCUMENTS

| | | | | |
|---|---|---|---|---|
| 4,654,796 A | * | 3/1987 | Takagi | .................. G06T 11/005 |
| | | | | 378/10 |
| 10,213,177 B2 | * | 2/2019 | Takahashi | .............. A61B 6/461 |
| 2021/0007694 A1 | * | 1/2021 | Hein | .................... A61B 6/4208 |

FOREIGN PATENT DOCUMENTS

| | | | | | |
|---|---|---|---|---|---|
| CN | 101109719 A | * | 1/2008 | ............. | A61B 6/488 |
| JP | 2003033348 A | * | 2/2003 | | |
| JP | 2016-106938 A | | 6/2016 | | |

OTHER PUBLICATIONS

Machine translation obtained from Google Patents of CN-101109719-A (Year: 2008).*

(Continued)

*Primary Examiner* — John Villecco
*Assistant Examiner* — Courtney Joan Nelson
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry acquires a plurality of projection data based on an output signal from an X-ray detector that rotates around a subject, performs reconstruction filter processing on the plurality of acquired projection data, the reconstruction filter processing being included in reconstruction regarding the plurality of projection data, generates correction information on a sensitivity difference area formed in the plurality of projection data due to differences in sensitivity of the X-ray detector, on the basis of a processing result of the reconstruction filter processing, performs correction processing on the plurality of projection data on the basis of the correction information, and performs reconstruction processing including the reconstruction filter processing on the plurality of projection data subjected to the correction processing.

10 Claims, 7 Drawing Sheets

(51) Int. Cl.
| | |
|---|---|
| *A61B 6/40* | (2024.01) |
| *G06T 5/70* | (2024.01) |
| *G06T 7/00* | (2017.01) |
| *G06T 11/00* | (2006.01) |
| *G16H 30/40* | (2018.01) |

(52) U.S. Cl.
CPC .......... *G06T 7/0012* (2013.01); *G06T 11/005* (2013.01); *G16H 30/40* (2018.01); *G06T 2207/10081* (2013.01); *G06T 2207/30004* (2013.01)

(58) Field of Classification Search
CPC .......... A61B 6/5217; A61B 2090/3764; A61B 6/4085; G06T 2207/10081; G06T 2207/30004; G06T 7/0012; G06T 11/005; G06T 2207/10116; G06T 5/70; G16H 30/40; G16H 50/30
See application file for complete search history.

(56) References Cited

OTHER PUBLICATIONS

Machine translation obtained from Google Patents of JP-2003033348-A (Year: 2003).*

\* cited by examiner

A1

A1

E1

MEDICAL IMAGE PROCESSING APPARATUS, X-RAY DIAGNOSTIC APPARATUS, AND MEDICAL IMAGE PROCESSING METHOD

CROSS-REFERENCE TO RELATED APPLICATIONS

This application is based upon and claims the benefit of priority from Japanese Patent Application No. 2022-143654, filed on Sep. 9, 2022, the entire contents of which are incorporated herein by reference.

FIELD

Embodiments described herein relate generally to a medical image processing apparatus, an X-ray diagnostic apparatus, and a medical image processing method.

BACKGROUND

In the related art, an X-ray diagnostic apparatus includes an X-ray detector that detects X-rays. When a part of the X-ray detector is continuously irradiated with X-rays, the X-ray sensitivity of the part irradiated with the X-rays may be changed. When the X-ray diagnostic apparatus reconstructs a three-dimensional volume image by using projection data generated in a state in which the X-ray sensitivity of the X-ray detector has changed, ring artifacts may occur.

DETAILED DESCRIPTION

A medical image processing apparatus according to an embodiment includes processing circuitry. The processing circuitry acquires a plurality of projection data based on an output signal from an X-ray detector that rotates around a subject, performs reconstruction filter processing on the plurality of acquired projection data, the reconstruction filter processing being included in reconstruction regarding the plurality of projection data, generates correction information on a sensitivity difference area formed in the plurality of projection data due to differences in sensitivity of the X-ray detector, on the basis of a processing result of the reconstruction filter processing, performs correction processing on the plurality of projection data on the basis of the correction information, and performs reconstruction processing including the reconstruction filter processing on the plurality of projection data subjected to the correction processing.

A medical image processing apparatus, an X-ray diagnostic apparatus, and a medical image processing method according to the present embodiment are described below with reference to the drawings. In the following embodiments, parts with the same reference signs are assumed to operate in the same way, and redundant descriptions thereof are omitted as appropriate.

First Embodiment

Figure 1:
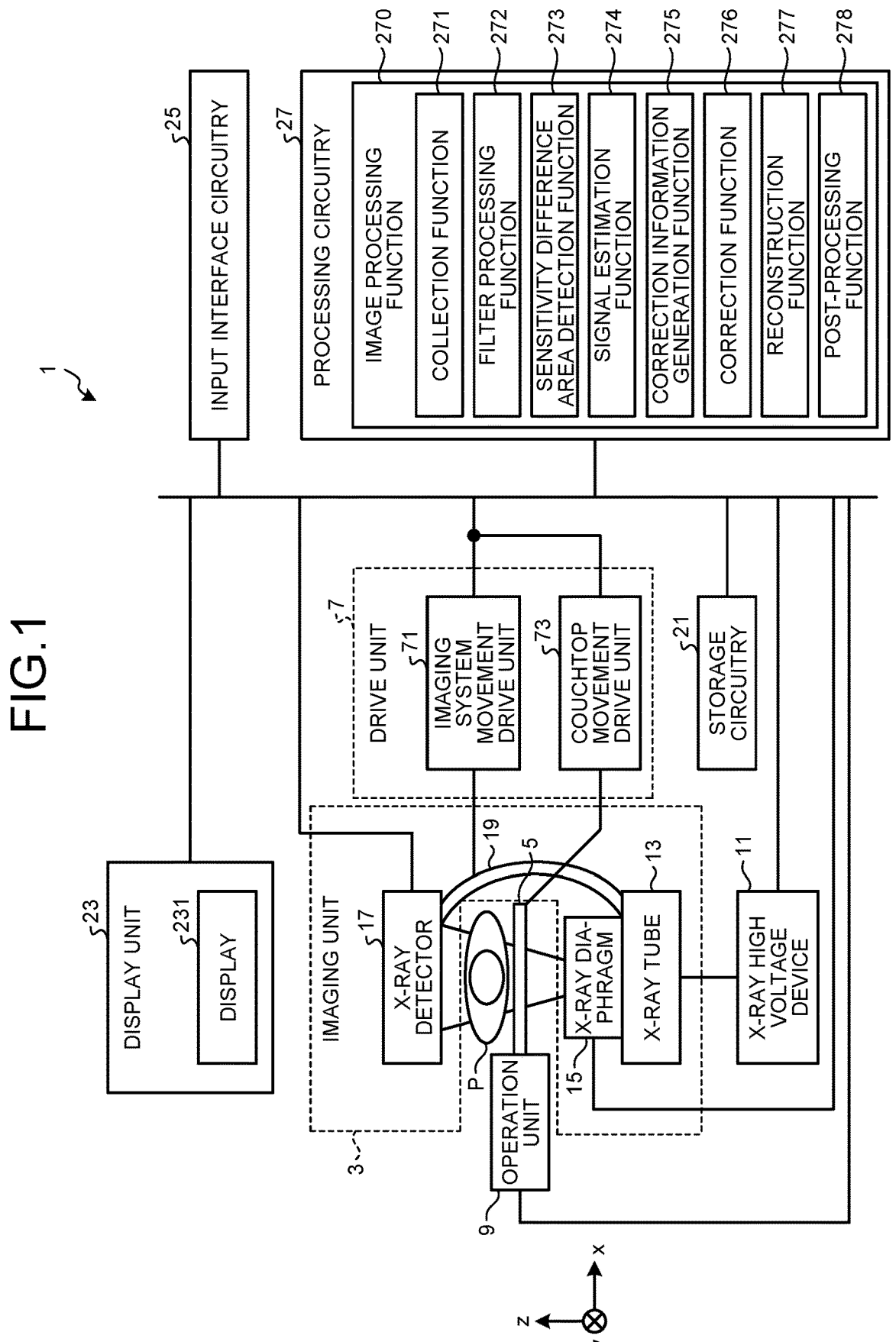
FIG. 1 is a diagram illustrating an example of the configuration of an X-ray diagnostic apparatus according to a first embodiment.

FIG. 1 is a diagram illustrating an example of the configuration of an X-ray diagnostic apparatus 1 according to a first embodiment. For the purpose of concrete explanation, an example in which the X-ray diagnostic apparatus 1 is an X-ray angiography apparatus is described below.

The X-ray diagnostic apparatus 1 includes an imaging unit 3, a table 5, a drive unit 7, an operation unit 9, an X-ray high voltage device 11, storage circuitry 21, a display unit 23, input interface circuitry 25, and processing circuitry 27.

The imaging unit 3 includes an X-ray tube 13 that irradiates a subject P (object) with X-rays, an X-ray detector 17 that detects X-rays, an X-ray diaphragm 15, and a support device 19. The imaging unit 3 is supported by the support device 19. The table 5 includes the operation unit 9 for operating the imaging unit 3 and the table 5.

The drive unit 7 drives the imaging unit 3 and the table 5. The drive unit 7 includes an imaging system movement drive unit 71 and a tabletop movement drive unit 73. The imaging system movement drive unit 71 drives the imaging unit 3 under the control of the processing circuitry 27 in order to move an imaging system such as the X-ray tube 13 and an X-ray detector 17 in a desired direction. The imaging system movement drive unit 71 is provided in the support device 19, for example, for each of a plurality of support members that support a plurality of components to be moved. The tabletop movement drive unit 73 drives the table 5 under the control of the processing circuitry 27 in order to move the table 5 (a tabletop 51) in a desired direction. The tabletop movement drive unit 73 is provided in the table 5, for example. The imaging system movement drive unit 71 and the tabletop movement drive unit 73 are each implemented by a motor, an actuator, or the like.

The X-ray high voltage device 11 includes electrical circuitry such as a transformer and a rectifier, a high voltage generator, and an X-ray control device. The high voltage generator has a function of generating a high voltage to be applied to the X-ray tube 13 and a filament current to be supplied to the X-ray tube 13. The X-ray control device controls an output voltage according to X-rays emitted by the X-ray tube 13. The high voltage generator may be of a transformer type or an inverter type. The X-ray high voltage device 11 may be provided in the support device 19.

The X-ray tube 13 is a vacuum tube that produces X-rays by emitting thermoelectrons from a cathode (filament) to an anode (target) by the application of a high voltage and the supply of a filament current from the X-ray high voltage device 11. The X-rays are produced by the impingement of the thermal electrons on the target. An example of the X-ray tube 13 includes a rotating anode type X-ray tube that produces X-rays by emitting thermoelectrons to a rotating anode. The X-ray tube 13 is not limited to the rotating anode type, and any type of X-ray tube can be applied.

The X-ray diaphragm 15 is provided in front of an X-ray radiation window in the X-ray tube 13. The X-ray diaphragm 15 has four diaphragm blades each made of a metal plate such as lead, for example. The diaphragm blades are driven by a drive device (not illustrated) according to the region of interest input by an operator via the operation unit 9 or the input interface circuitry 25. The X-ray diaphragm 15 adjusts an X-ray blocking area to any size by sliding these diaphragm blades by the drive device. With the adjusted diaphragm blades, the X-ray diaphragm 15 blocks X-rays outside an aperture area. Thus, the X-ray diaphragm 15 narrows down X-rays produced by the X-ray tube 13 so that the region of interest of the subject P is irradiated with the X-rays.

The X-ray detector 17 detects X-rays produced by the X-ray tube 13. The X-ray detector 17 is, for example, a flat panel detector (hereinafter, referred to as FPD). The FPD has a plurality of semiconductor detection elements. The semiconductor detection elements are classified into two types: a direct conversion system that directly converts X-rays into electrical signals and an indirect conversion system that converts X-rays into light using phosphors and converts the light into electrical signals. Any of the systems may be used for the FPD. The electrical signals generated by the plurality of semiconductor detection elements resulting from the incidence of X-rays are output to an analog-to-digital converter (hereinafter, referred to as A/D converter) (not illustrated). The A/D converter converts electrical signals into digital data. The A/D converter outputs the digital data to the processing circuitry 27. An image intensifier may be used as the X-ray detector 17.

The support device 19 is a C-shaped arm that holds the X-ray tube 13/the X-ray diaphragm 15 and the X-ray detector 17 to face each other with the subject P interposed therebetween. The support device 19 rotationally moves around the subject P lying on the table 5 by a motor (not illustrated). The support device 19 is rotatably supported about XYZ axes, which are three orthogonal axes, and is rotated about each axis by a drive unit (not illustrated).

The storage circuitry 21 is a storage device such as a hard disk drive (HDD), a solid state drive (SSD), or an integrated circuit storage device that stores various information. The storage circuitry 21 stores, for example, projection data, image data, and computer programs corresponding to various functions that are read and executed by the processing circuitry 27. In addition to the HDD, the SSD, and the like, the storage circuitry 21 may also be a drive device that reads and writes various information from/to a portable storage medium such as a compact disc (CD), a digital versatile disc (DVD), and a flash memory, a semiconductor memory element such as a random access memory (RAM), and the like. A storage area of the storage circuitry 21 may be in an external storage device connected by a network.

The display unit 23 includes a display 231 that displays medical images or the like, internal circuitry that supplies display signals to the display 231, and peripheral circuitry such as connectors and cables that connect the display 231 and the internal circuitry. The internal circuitry generates display data by superimposing supplementary information such as subject information and projection data generation conditions on image data. Subsequently, the internal circuitry performs D/A conversion and TV format conversion on the obtained display data. The internal circuitry displays the display data subjected to these conversions on the display 231 as a medical image. In addition to this, the display unit 23 displays, for example, a graphical user interface (GUI) for receiving various operations from an operator.

Examples of the display 231 that can be appropriately used include a liquid crystal display (LCD), a cathode ray tube (CRT) display, an organic electro luminescence display (OELD), a plasma display, and any other displays. The display 231 may be of a desktop type, or may be configured by a tablet terminal or the like capable of wirelessly communicating with the processing circuitry 27.

The input interface circuitry 25 receives various input operations from an operator, converts the received input operations into electric signals, and outputs the electric signals to the processing circuitry 27. For example, the input interface circuitry 25 receives, from an operator, operations for operating at least one of the imaging unit 3 and the table 5, X-ray conditions related to X-ray production, conditions related to image processing performed by an image processing function 270, and the like. Examples of the input interface circuitry 25 that can be appropriately used include a mouse, a keyboard, a trackball, a switch, a button, a joystick, a foot switch, a touch pad, and a touch panel display. The input interface circuitry 25 is mounted, for example, on a console device 10 installed in an operation room different from an examination room.

Note that in the present embodiment, the input interface circuitry 25 is not limited to those with physical operating components such as a mouse, a keyboard, a trackball, a switch, a button, a joystick, a touch pad, and a touch panel display. An example of the input interface circuitry 25 also includes electrical signal processing circuitry that receives electrical signals corresponding to input operations from an external input device provided separately from the apparatus and outputs the electrical signals to the processing circuitry 27. Note that the input interface circuitry 25 may also be configured by a tablet terminal or the like capable of wirelessly communicating with the processing circuitry 27.

The processing circuitry 27 controls the operation of the entire X-ray diagnostic apparatus 1. The processing circuitry 27 has, for example, the image processing function 270. The image processing function 270 has a collection function 271, a filter processing function 272, a sensitivity difference area detection function 273, a signal estimation function 274, a correction information generation function 275, a correction function 276, a reconstruction function 277, and a post-processing function 278. In the embodiment, processing functions performed by the image processing function 270 is stored in the storage circuitry 21 in the form of computer programs executable by a computer. The processing circuitry 27 is a processor that reads the computer programs from the storage circuitry 21 and executes the read computer programs, thereby implementing the functions corresponding to the executed computer programs. In other words, the processing circuitry 27 in the state of reading the computer programs has the functions illustrated in the processing circuitry 27 in FIG. 1.

In FIG. 1, the image processing function 270 described as being implemented by a single piece of processor; however, a plurality of independent processors may be combined to form the processing circuitry 27 and the functions may be implemented by each processor executing the computer program. In FIG. 1, single piece of storage circuitry such as the storage circuitry 21 is described as storing the computer programs corresponding to the respective processing functions; however, a plurality of pieces of storage circuitry may be distributedly disposed and the processing circuitry 27 may be configured to read each computer program from each storage circuitry.

The term "processor" used in the above description, for example, means circuitry such as a central processing unit (CPU), a graphics processing unit (GPU), an application specific integrated circuit (ASIC), or a programmable logic device (for example, a simple programmable logic device (SPLD), a complex programmable logic device (CPLD), and a field programmable gate array (FPGA)). The processor implements functions by reading and executing the computer programs stored in the storage circuitry 21. Instead of storing the computer programs in the storage circuitry 21, the computer programs may be directly incorporated in the circuitry of the processor. In this case, the processor implements the functions by reading and executing the computer programs incorporated in the circuitry.

In such a configuration, the X-ray diagnostic apparatus 1 generates projection data on the basis of detection results of the X-ray detector 17. The X-ray diagnostic apparatus 1 also has a corn beam computed tomography (CBCT) function of reconstructing a three-dimensional volume image by using a computed tomography technology from projection data collected while the X-ray detector 17 supported by the support device 19 is rotated around the subject P.

When the X-ray detector 17 is continuously irradiated with X-rays for a certain period of time, the X-ray detection sensitivity at a portion irradiated with the X-rays is changed. That is, in the X-ray detector 17, differences in sensitivity occur between the portion continuously irradiated with the X-rays for a certain period of time and other portions.

Figure 2A:
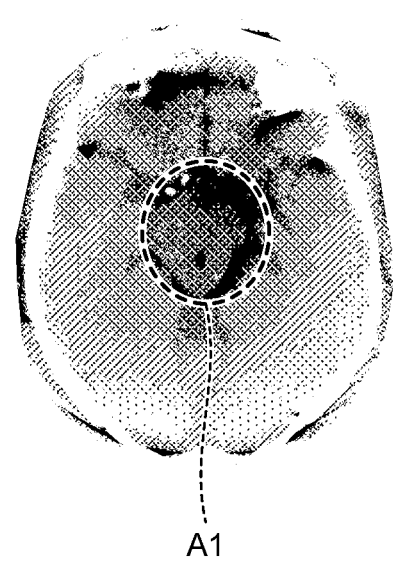
FIG. 2A is a diagram illustrating an example of a three-dimensional volume image with ring artifacts.
Figure 2B:
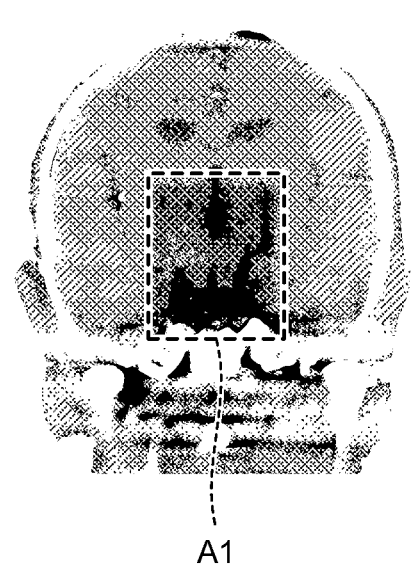
FIG. 2B is a diagram illustrating an example of a three-dimensional volume image with ring artifacts.

When the X-ray diagnostic apparatus 1 reconstructs a three-dimensional volume image by using projection data based on the detection results of the X-ray detector 17 having differences in the sensitivity, artifacts such as ring artifacts appear in the three-dimensional volume image. FIG. 2A is a diagram illustrating an example of a three-dimensional volume image with ring artifacts. FIG. 2A is a cross-sectional image of a plane perpendicular to the body axis direction of the subject P. FIG. 2B is a diagram illustrating an example of a three-dimensional volume image with ring artifacts. FIG. 2B is a cross-sectional image of a coronal plane of the subject P. As illustrated in FIGS. 2A and 2B, a cylindrical artifact A1 having a cylindrical shape appears in the three-dimensional volume image. Therefore, the X-ray diagnostic apparatus 1 suppresses artifacts due to differences in the sensitivity by the following functions.

The collection function 271 collects a plurality of projection data on the basis of output signals from the X-ray detector 17 that rotates around the subject P. The collection function 271 is an example of a collection unit. More specifically, the collection function 271 generates the plurality of projection data on the basis of respective detection results at a plurality of rotation angles by the X-ray detector 17 that rotates around the subject P in the CBCT function.

The collection function 271 stores the plurality of collected projection data in the storage circuitry 21. That is, the collection function 271 is an example of a storage control unit.

The filter processing function 272 performs various types of filter processing on the plurality of projection data collected by the collection function 271. More specifically, the filter processing function 272 performs reconstruction filter processing, which is included in reconstruction regarding the plurality of projection data, on the plurality of projection data acquired by the collection function 271. In other words, the filter processing function 272 performs reconstruction filter processing on the plurality of projection data collected by the collection function 271 to emphasize a sensitivity difference area D1 formed in the plurality of projection data due to differences in the sensitivity of the X-ray detector 17. The filter processing function 272 is an example of a filter processing unit.

When the X-ray detector 17 is continuously irradiated with X-rays for a certain period of time, the sensitivity of a detection element at a portion irradiated with the X-rays is changed. The sensitivity difference area D1 is an area generated on the basis of output signals from the detection element whose X-ray sensitivity has changed. The sensitivity difference area D1 is an area where a signal value is abnormal due to differences in the sensitivity.

The reconstruction filter processing is a process performed in reconstruction processing of generating three-dimensional volume data from the plurality of projection data, and has the effect of emphasizing high-frequency components of the projection data. That is, the reconstruction filter processing is performed using the same reconstruction function as a reconstruction function used in the reconstruction processing performed by the reconstruction function 277. Such reconstruction filter processing can employ a filter using a ramp function or a Shepp-Logan filter.

The filter processing function 272 further performs averaging processing on the plurality of projection data subjected to the reconstruction filter processing. The averaging processing is a process of averaging signals of each pixel based on the detection results of the same detection element in the plurality of projection data. In the plurality of projection data, the signals of each pixel have different values, but are equalized by the averaging processing. The sensitivity difference area D1 appears at the same position in the projection data because it is generated due to differences in the sensitivity of the X-ray detector 17. Thus, the sensitivity difference area D1 is emphasized by equalizing the signal values through the averaging processing.

Figure 3:
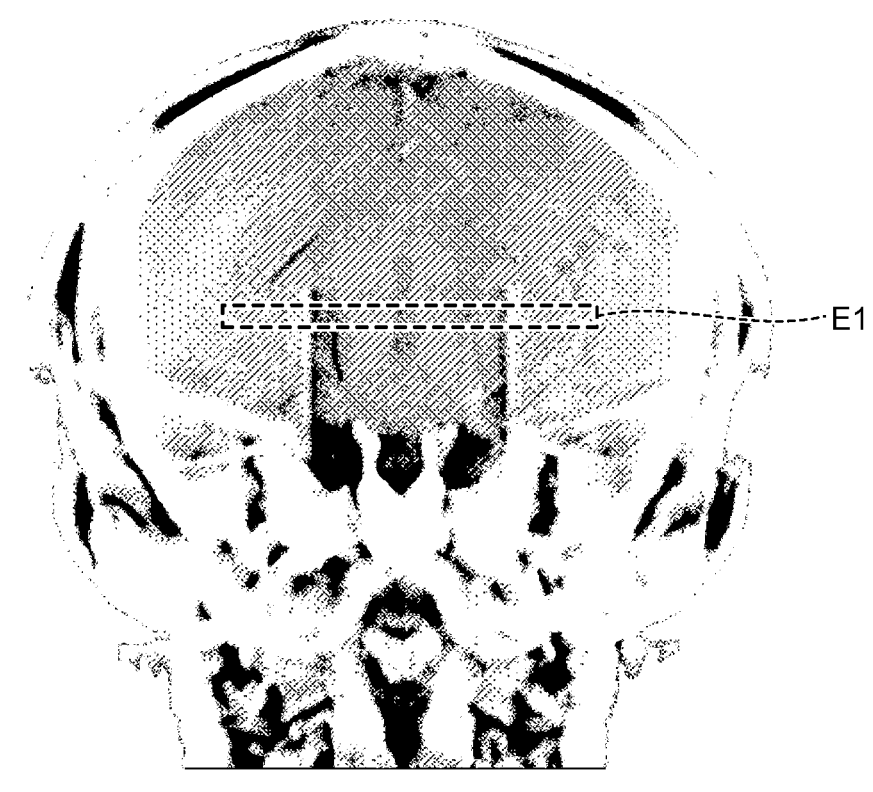
FIG. 3 is a diagram illustrating an example of an image resulting from averaging processing.

The sensitivity difference area detection function 273 detects the sensitivity difference area D1 on the basis of the processing results of the averaging processing performed on the plurality of projection data. FIG. 3 is a diagram illustrating an example of an image resulting from averaging processing; As illustrated in FIG. 3, the sensitivity difference area detection function 273 sets a search area E1 for the image resulting from the averaging processing. The search area E1 is an area where the sensitivity difference area detection function 273 searches for the sensitivity difference area D1.

Figure 4:
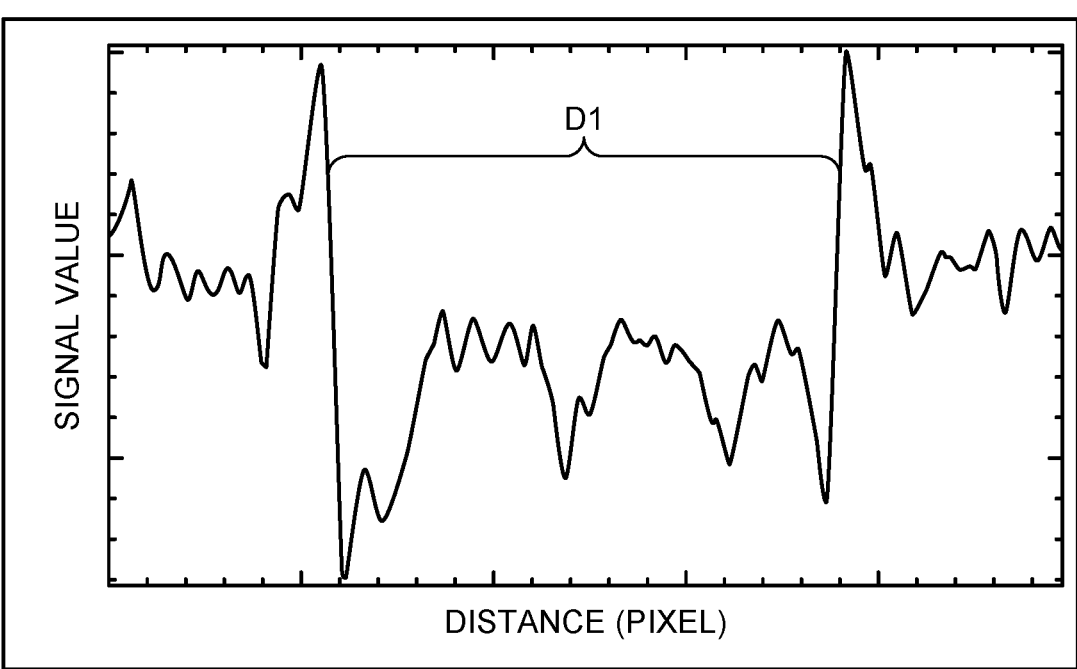
FIG. 4 is a profile showing the signal values of each pixel in a search area illustrated in FIG. 3.

FIG. 4 is a profile showing the signal values of each pixel in the search area E1 illustrated in FIG. 3. When the sensitivity difference area D1 is included in the search area E1, the signal values of each pixel in the sensitivity difference area D1 have a difference due to differences in the sensitivity compared to signal values in an area other than the sensitivity difference area D1. Therefore, the sensitivity difference area detection function 273 performs edge detection processing and change point detection processing. The edge detection processing is a process of detecting an edge indicating a boundary between the sensitivity difference area D1 and an area other than the sensitivity difference area D1. The change point detection processing is a process of regarding the profile in FIG. 4 as one signal and detecting a change point where the sensitivity difference area D1 and the area other than sensitivity difference area D1 are switched. In this way, the sensitivity difference area detection function 273 detects the sensitivity difference area D1 from the search area E1 by detecting boundaries and change points.

The sensitivity difference area detection function 273 further sets the search area E1 for all areas of the processing results of the averaging processing, and performs a process of detecting the sensitivity difference area D1 from the search area E1. Thus, the sensitivity difference area detection function 273 detects the sensitivity difference area D1 from all the areas of the processing results of the averaging processing.

The signal estimation function 274 estimates a signal value when there are no differences in sensitivity in the sensitivity difference area D1 detected by the sensitivity difference area detection function 273. The signal estimation function 274 is an example of an estimation unit. For example, on the basis of the signal values in the area other than the sensitivity difference area D1, the signal estimation function 274 estimates a signal value when there are no differences in sensitivity in the sensitivity difference area D1.

Figure 5:
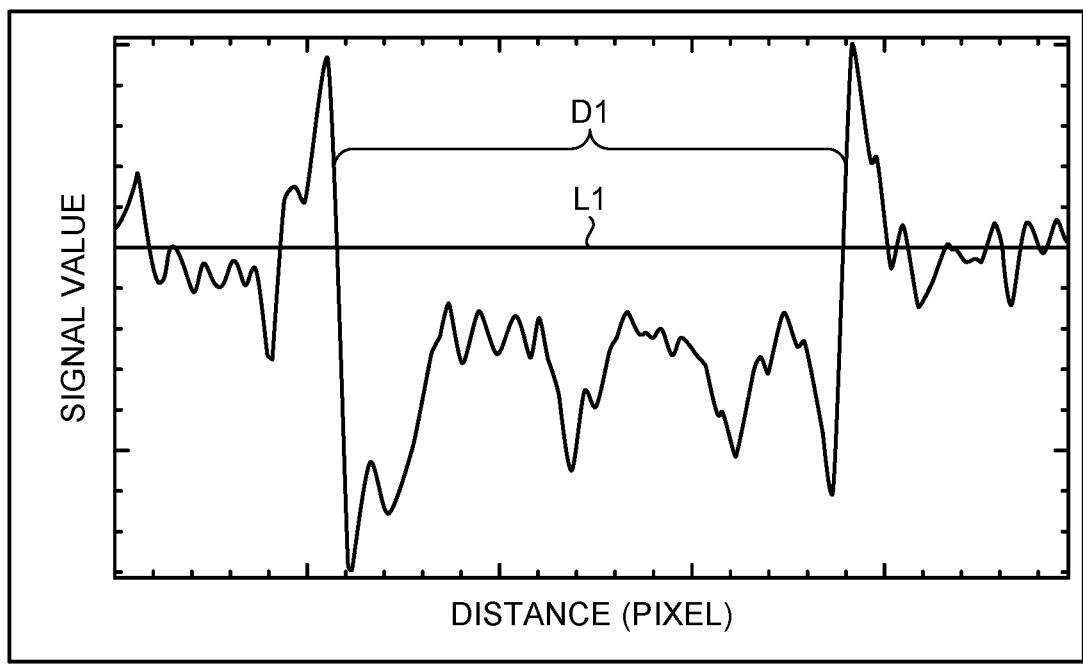
FIG. 5 is a diagram illustrating an example of a signal value estimation method.

FIG. 5 is a diagram illustrating an example of a signal value estimation method. For example, the signal estimation function 274 estimates signal values by linear interpolation. FIG. 5 illustrates a state in which a line L1 indicated by a function is set in the profile indicating the signal values of each pixel in the search area E1 illustrated in FIG. 4. The signal estimation function 274 calculates a function that approximates the signal values of each pixel in an area other than the sensitivity difference area D1. Subsequently, the signal estimation function 274 estimates that a value indicated by the sensitivity difference area D1 on the line L1 indicated by the calculated function is the signal value in the sensitivity difference area D1. The signal estimation function 274 may estimate a signal value for each pixel or a signal value for each of a plurality of pixels.

The signal estimation function 274 may also estimate a signal value by other methods as well as the linear interpolation.

The signal estimation function 274 may estimate that a signal value of a portion of the subject P specified by a portion of the subject P to which the sensitivity difference area D1 belongs is the signal value when there are no differences in sensitivity in the sensitivity difference area D1. For example, when the sensitivity difference area D1 is formed in a soft tissue portion of a head, the signal estimation function 274 extracts the soft tissue portion of the head as a portion corresponding to the soft tissue portion of the head. Specifically, the head has the skull on the outside and the brain, that is, a soft tissue portion, on the inside. The soft tissue portion has a small variation in density distribution. Therefore, the signal estimation function 274 extracts the soft tissue portion of the head. Subsequently, the signal estimation function 274 estimates that signal value in an area, other than the sensitivity difference area D1, within the soft tissue portion of the head is the signal value when there are no differences in sensitivity in the sensitivity difference area D1.

When bone exists in the sensitivity difference area D1, the signal estimation function 274 may also stop estimating the signal value in the sensitivity difference area D1. In this case, the signal estimation function 274 estimates that a signal value estimated in the search area E1 closest to the search area E1 where the signal value estimation has been stopped is the signal value when there are no differences in sensitivity in the sensitivity difference area D1 included in the search area E1 where the signal value estimation has been stopped.

Alternatively, in the signal estimation function 274, when bones and soft tissues are mixed in the sensitivity difference area D1, such as in the abdomen of the subject P, the distribution of signal values in the sensitivity difference area D1 is complicated. Therefore, the signal estimation function 274 selects a model to approximate according to complexity. Subsequently, on the basis of the selected model, the signal estimation function 274 may estimate the signal value when there are no differences in sensitivity in the sensitivity difference area D1.

On the basis of the processing results of the filter processing function 272, the correction information generation function 275 generates correction information on the sensitivity difference area D1 formed in the plurality of projection data due to differences in the sensitivity of the X-ray detector 17. In other words, on the basis of the processing results of the filter processing function 272, the correction information generation function 275 generates correction information indicating at least correction details for the sensitivity difference area D1. The correction information generation function 275 is an example of a generation unit. The correction information includes position information and signal values. The position information is information indicating the position of the sensitivity difference area D1 detected by the sensitivity difference area detection function 273 on the basis of the processing results of the filter processing function 272. The signal values are the signal values of each pixel in the sensitivity difference area D1 estimated by the signal estimation function 274. In other words, the correction information generation function 275 generates correction information on the basis of the estimation results of the signal estimation function 274.

The correction function 276 performs correction processing on the plurality of projection data on the basis of the correction information generated by the correction information generation function 275. The correction function 276 is an example of a correction unit. The correction processing is a process of correcting the signal values of each pixel in an area specified by the correction information to signal values included in the correction information.

For example, on the basis of the correction information, the correction function 276 performs the correction processing on the plurality of projection data stored in the storage circuitry 21 by the collection function 271. That is, the correction function 276 acquires the plurality of projection data from the storage circuitry 21. Subsequently, the correction function 276 performs the correction processing on each of the plurality of acquired projection data.

The reconstruction function 277 performs the reconstruction processing, including the same reconstruction filter processing as the reconstruction filter processing performed by the filter processing function 272, on the plurality of projection data subjected to the correction processing by the correction function 276. The reconstruction function 277 is an example of a reconstruction unit. The reconstruction function 277 generates CT image data, that is, three-dimensional volume images, by performing the reconstruction processing. Furthermore, since the reconstruction function 277 performs the reconstruction processing including the same reconstruction filter processing as reconstruction filter processing to be performed by the filter processing function 272, the sensitivity difference area D1 can be suppressed from becoming apparent in the reconstruction processing.

Figure 6:
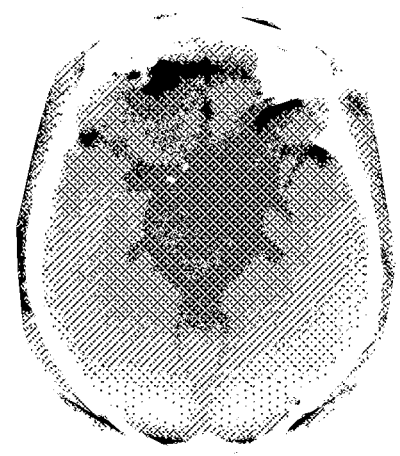
FIG. 6 is a diagram illustrating an example of a three-dimensional volume image with ring artifacts corrected.

FIG. 6 is a diagram illustrating an example of a three-dimensional volume image with ring artifacts corrected. As illustrated in FIG. 6, the cylindrical artifact A1 that appeared in FIGS. 2A and 2B has been reduced to disappear. In this way, the reconstruction function 277 generates a three-dimensional volume image in which artifacts are reduced by performing the correction processing.

The post-processing function 278 performs post-processing on the CT image data generated by the reconstruction function 277. For example, the post-processing is a process of analyzing a portion of the subject P included in the CT image data.

The generation processing of generating the three-dimensional volume image by the X-ray diagnostic apparatus 1 is described below.

Figure 7:
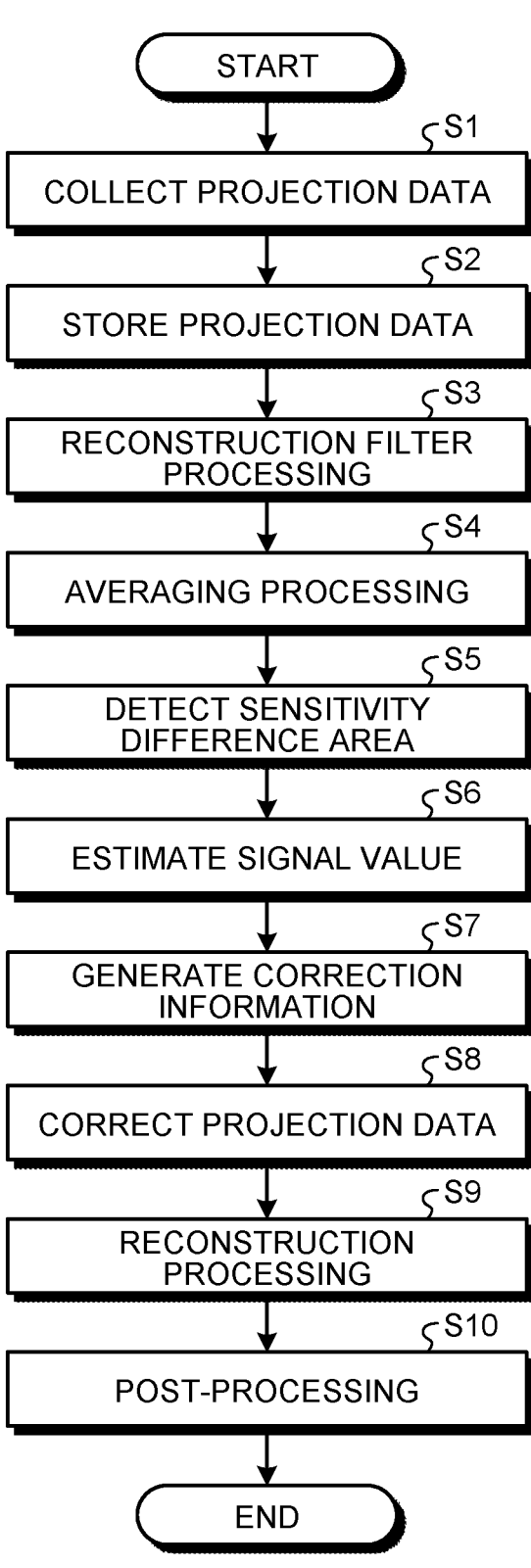
FIG. 7 is a flowchart illustrating an example of generation processing performed by the X-ray diagnostic apparatus according to the first embodiment.

FIG. 7 is a flowchart illustrating an example of the generation processing performed by the X-ray diagnostic apparatus 1 according to the first embodiment.

The collection function 271 collects a plurality of projection data on the basis of output signals from the X-ray detector 17 (step S1).

The collection function 271 stores the plurality of collected projection data in a storage medium such as the storage circuitry 21 (step S2).

The filter processing function 272 performs reconstruction filter processing on the plurality of projection data collected by the collection function 271 (step S3).

The filter processing function 272 performs averaging processing on the plurality of projection data subjected to the reconstruction filter processing (step S4).

The sensitivity difference area detection function 273 detects the sensitivity difference area D1 on the basis of the processing results of the averaging processing (step S5).

The signal estimation function 274 estimates a signal value when there are no differences in sensitivity in the sensitivity difference area D1 (step S6).

The correction information generation function 275 generates correction information indicating correction details for the sensitivity difference area D1 on the basis of the processing results of the filter processing function 272 (step S7).

The correction function 276 performs the correction processing on the plurality of projection data stored in the storage circuitry 21 by the collection function 271, on the basis of the correction information (step S8).

Note that the sensitivity difference area D1 is not limited to one, and a plurality of sensitivity difference areas D1 may be generated. In this case, the X-ray diagnostic apparatus 1 may proceed to step S5. By repeating this process, the X-ray diagnostic apparatus 1 can correct a plurality of sensitivity difference areas D1 in turn from the inside or outside of the projection data.

The reconstruction function 277 performs the reconstruction processing, including the same reconstruction filter processing as the reconstruction filter processing performed by the filter processing function 272, on the plurality of projection data subjected to the correction processing by the correction function 276 (step S9).

The post-processing function 278 performs post-processing (step S10).

With the above, the X-ray diagnostic apparatus 1 ends the generation processing.

As described above, the X-ray diagnostic apparatus 1 according to the first embodiment collects a plurality of projection data based on output signals from the X-ray detector 17 that rotates around the subject P. The X-ray diagnostic apparatus 1 performs reconstruction filter processing on the plurality of collected projection data to emphasize the sensitivity difference area D1 formed in the plurality of projection data due to differences in the sensitivity of the X-ray detector 17. On the basis of the processing results of the reconstruction filter processing, the X-ray diagnostic apparatus 1 generates correction information indicating correction details for the sensitivity difference area D1. The X-ray diagnostic apparatus 1 performs the correction processing on the plurality of projection data on the basis of the correction information. Subsequently, the X-ray diagnostic apparatus 1 performs the reconstruction processing, including the same reconstruction filter processing as the reconstruction filter processing performed to emphasize the sensitivity difference area D1, on the plurality of projection data subjected to the correction processing. Thus, the X-ray diagnostic apparatus 1 can correct the sensitivity difference area D1 that causes artifacts. Consequently, the X-ray diagnostic apparatus 1 can suppress artifacts due to differences in the sensitivity of the X-ray detector 17.

Moreover, the X-ray diagnostic apparatus 1 performs the same reconstruction filter processing as the reconstruction filter processing performed in the reconstruction processing in order to emphasize the sensitivity difference area D1. Consequently, the X-ray diagnostic apparatus 1 can suppress the appearance of artifacts due to the sensitivity difference area D1 becoming apparent in the reconstruction processing, in three-dimensional volume data.

Moreover, the X-ray diagnostic apparatus 1 performs the correction processing on a plurality of projection data stored in the storage circuitry 21. Therefore, the X-ray diagnostic apparatus 1 can reduce the processing load compared to when inverse filter processing is performed on the processing results of the filter processing function 272 to return to the state before the processing.

Second Embodiment

Figure 8:
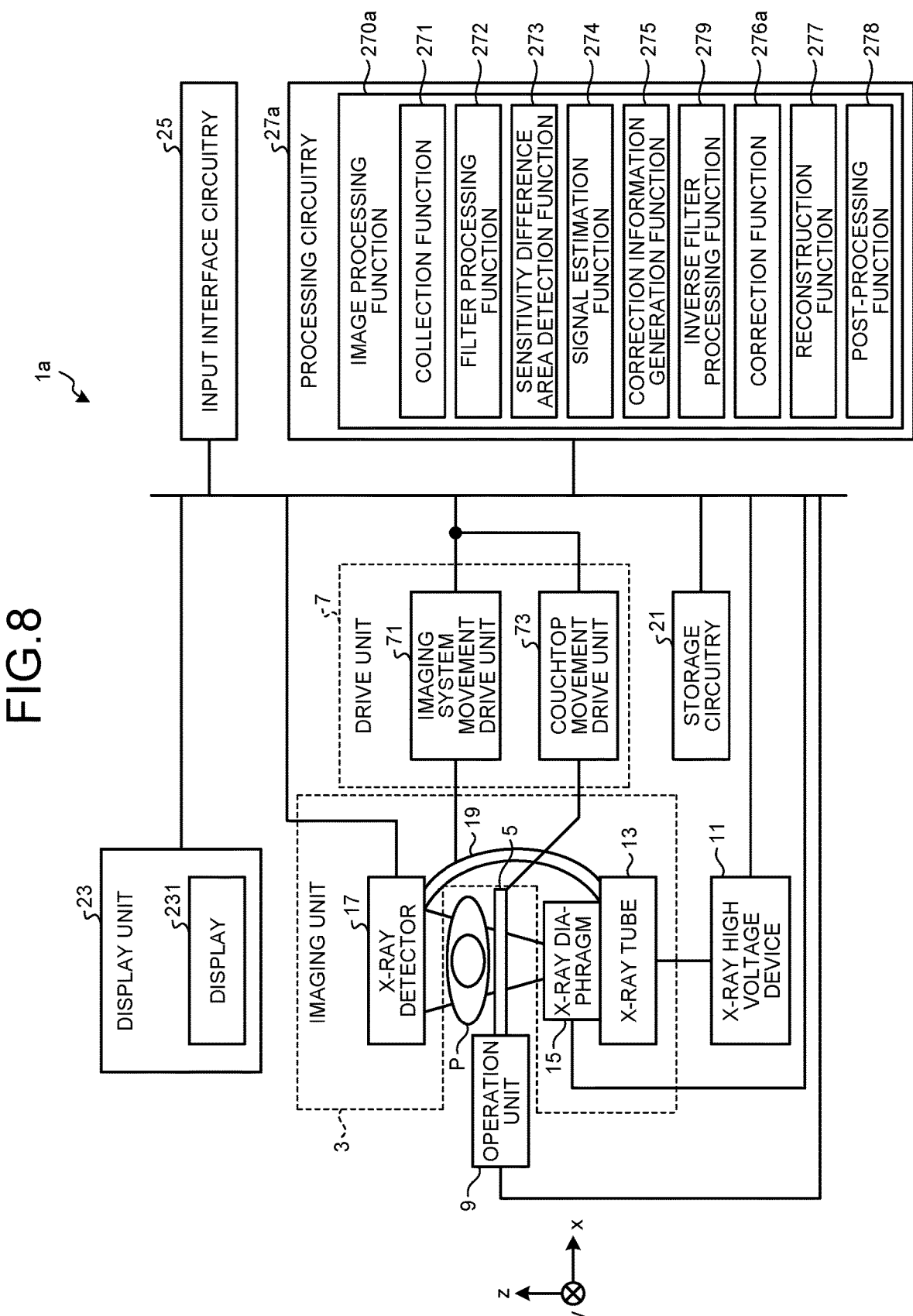
FIG. 8 is a block diagram illustrating an example of the configuration of an X-ray diagnostic apparatus according to a second embodiment.

FIG. 8 is a block diagram illustrating an example of the configuration of an X-ray diagnostic apparatus 1a according to a second embodiment.

An image processing function 270a of processing circuitry 27a of the X-ray diagnostic apparatus 1a has an inverse filter processing function 279.

The inverse filter processing function 279 performs inverse filter processing on the processing results of the filter processing function 272 to return to the state before the processing. That is, the inverse filter processing function 279 performs inverse filter processing on the processing results of the reconstruction filter processing by the filter processing function 272 to return to the state before the reconstruction filter processing is performed. The inverse filter processing function 279 is an example of an inverse filter processing unit. The inverse filter processing function 279 further performs inverse filter processing on the processing results of the averaging processing by the filter processing function 272 to return to the state before the averaging processing is performed.

More specifically, the inverse filter processing function 279 performs first inverse filter processing on the processing result of the averaging processing by the filter processing function 272 to return to the plurality of projection data before the averaging processing is performed. The inverse filter processing function 279 further performs second inverse filter processing on the processing results of the first inverse filter processing to return to the plurality of projection data before the reconstruction filter processing is performed. Thus, the inverse filter processing function 279 generates a plurality of projection data before the reconstruction filter processing and the averaging processing are performed by the filter processing function 272.

A correction function 276a performs the correction processing on the plurality of projection data generated by the inverse filter processing. That is, the correction function 276a performs the correction processing on the plurality of projection data generated by the inverse filter processing function 279 and before the reconstruction filter processing and the averaging processing are performed. More specifically, the correction function 276a performs the correction processing on each of the plurality of projection data generated by the second inverse filter processing.

The reconstruction function 277 performs the reconstruction processing, including the same reconstruction filter processing as the reconstruction filter processing performed by the filter processing function 272, on the plurality of projection data subjected to the correction processing by the correction function 276a.

As described above, the X-ray diagnostic apparatus 1a according to the second embodiment performs inverse filter processing on the processing results of the reconstruction filter processing by the filter processing function 272 to return to the state before the reconstruction filter processing is performed. Subsequently, the X-ray diagnostic apparatus 1a performs the correction processing on the plurality of projection data generated by the inverse filter processing. Consequently, the storage circuitry 21 does not need to store the plurality of projection data collected by the collection function 271. Thus, the X-ray diagnostic apparatus 1a can reduce the storage capacity of the storage circuitry 21.

Third Embodiment

Figure 9:
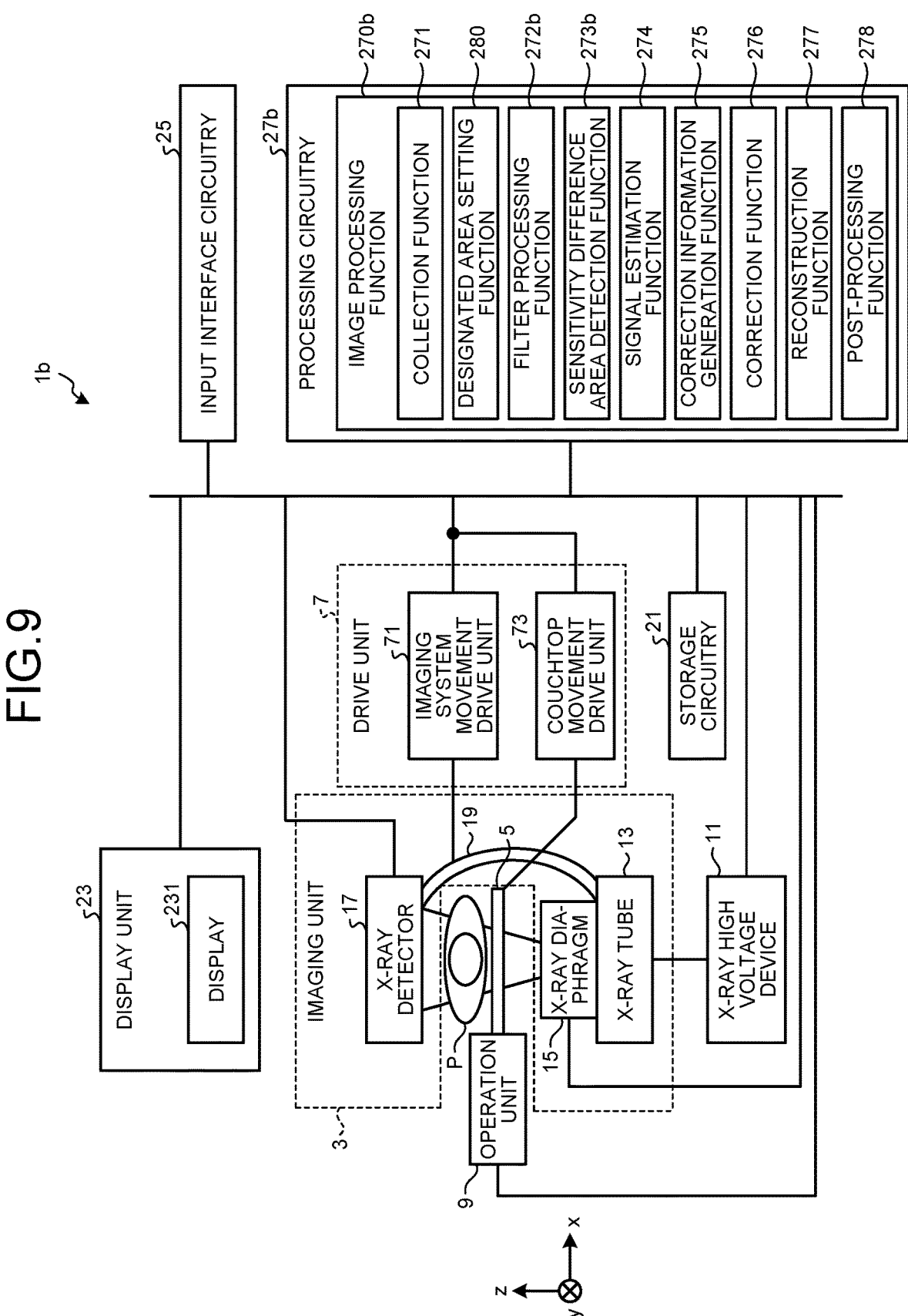
FIG. 9 is a block diagram illustrating an example of the configuration of an X-ray diagnostic apparatus according to a third embodiment.

FIG. 9 is a block diagram illustrating an example of the configuration of an X-ray diagnostic apparatus 1b according to a third embodiment.

An image processing function 270b of processing circuitry 27b of the X-ray diagnostic apparatus 1b has a designated area setting function 280.

The designated area setting function 280 designates an area where the sensitivity difference area D1 is searched. The designated area setting function 280 is an example of a designation unit. More specifically, the designated area setting function 280 sets a designated area as the area where the sensitivity difference area D1 is searched. The designated area setting function 280 narrows down the area where the sensitivity difference area D1 is searched by setting the designated area. Subsequently, the X-ray diagnostic apparatus 1b performs a process of searching for the sensitivity difference area D1 on the designated area.

For example, the designated area setting function 280 sets the designated area on the basis of the X-ray irradiation history of X-ray irradiation by the X-ray diagnostic apparatus 1b. The X-ray irradiation history is information indicating, for example, the time of X-ray irradiation and the field of view in which X-rays were irradiated. On the basis of the X-ray irradiation history, the designated area setting function 280 estimates an area where a sensitivity difference changes. Subsequently, the designated area setting function 280 sets an area including the estimated area as the designated area.

For example, the designated area setting function 280 receives an operation for defining the designated area. Subsequently, the designated area setting function 280 sets an area specified by the operation as the designated area.

For example, the designated area setting function 280 sets the designated area on the basis of projection data collected in the absence of the subject P. The signal values of each pixel included in the projection data vary depending on the subject P. Thus, the signal value of each pixel in the projection data collected in the absence of the subject P is a constant value because it is not affected by the subject P.

That is, when the subject P is present, the X-ray diagnostic apparatus 1b has a difficulty in determining whether the signal values of each pixel are caused by differences in sensitivity or the influence of the subject P. However, when the subject P is not present, the signal values of each pixel are caused by differences in sensitivity because there is no possibility of being affected by subject P. Therefore, the designated area setting function 280 can detect an area where the sensitivity difference is changing from the projection data collected in the absence of the subject P. Subsequently, the designated area setting function 280 sets an area including the detected area as the designated area.

A filter processing function 272b performs reconstruction filter processing on the designated area set by the designated area setting function 280 in the plurality of projection data collected by the collection function 271. The filter processing function 272b further performs averaging processing on the designated area set by the designated area setting function 280 in the plurality of projection data subjected to the reconstruction filter processing.

A sensitivity difference area detection function 273b detects the sensitivity difference area D1 from the processing results of the averaging processing. The averaging processing is performed on the designated area of the plurality of projection data. That is, the sensitivity difference area detection function 273b sets the search area E1 for all areas of the designated area. Subsequently, the sensitivity difference area detection function 273b detects the sensitivity difference area D1 from the designated area.

An area where the sensitivity difference area D1 is highly likely to occur is set as the designated area. Therefore, when the sensitivity difference area D1 is not able to be detected from the designated area, the sensitivity difference area detection function 273b may relax the conditions for detecting the sensitivity difference area D1 in the edge detection processing or the change point detection processing.

Alternatively, when the sensitivity difference area detection function 273b is unable to detect the sensitivity difference area D1 from the designated area, the designated area setting function 280 may request re-setting of the designated area. In this case, the filter processing function 272b performs reconstruction filter processing and averaging processing on a re-set designated area. The sensitivity difference area detection function 273b detects the sensitivity difference area D1 from the re-set designated area. In this way, the sensitivity difference area detection function 273b can suppress erroneous detection by detecting the sensitivity difference area D1 from the designated area.

As described above, the X-ray diagnostic apparatus 1b according to the third embodiment designates an area where the sensitivity difference area D1 is searched. The X-ray diagnostic apparatus 1b performs reconstruction filter processing on a designated area in a plurality of collected projection data.

In this way, the X-ray diagnostic apparatus 1b can reduce the processing time by narrowing down an area to be subjected to the reconstruction filter processing. Moreover, since the sensitivity difference area D1 is highly likely to exist in the designated area, the X-ray diagnostic apparatus 1b can appropriately relax the conditions for detecting the sensitivity difference area D1. Consequently, the X-ray diagnostic apparatus 1b can improve the accuracy of detecting the sensitivity difference area D1.

First Modification

The X-ray diagnostic apparatuses 1, 1*a*, and 1*b* each include the X-ray detector 17 with different structures depending on the part. Specifically, the X-ray detector 17 may have a structure with different resolutions and sensitivities depending on the part.

For example, the X-ray detector 17 includes a high-resolution area with a high resolution at approximately the center where X-rays are irradiated and a low-resolution area with a lower resolution than the resolution of the high-resolution area. The X-ray detector 17 includes a scintillator that converts X-rays into light and a photodetector that detects the light converted by the scintillator. The X-ray detector 17 converts the light detected by the photodetector into electrical signals, and outputs the electrical signals to the processing circuitry 27, 27*a* and 27*b*.

The X-ray detector 17 implements the high-resolution area and the low-resolution area by disposing different photodetectors depending on the area on an X-ray detection surface thereof. However, since the structure of such an X-ray detector 17 differs for each region, differences in sensitivity may occur.

The collection function 271 collects a plurality of projection data based on output signals from the X-ray detector 17 with different resolutions depending on the part. In other words, the collection function 271 acquires the plurality of projection data based on the output signals from the X-ray detector 17 with different resolutions depending on the part. Subsequently, the filter processing functions 272 and 272*b*, the sensitivity difference area detection functions 273 and 273*b*, the signal estimation function 274, the correction information generation function 275, the correction function 276, the reconstruction function 277, the post-processing function 278, the inverse filter processing function 279, and the designated area setting function 280 perform respective processes. Thus, the X-ray diagnostic apparatuses 1, 1*a*, and 1*b* can also correct differences in sensitivity due to different structures depending on the area of the X-ray detector 17.

As described above, since the X-ray detector 17 has different structures depending on the part on an X-ray detection surface thereof, even when differences in X-ray sensitivity occur, the X-ray diagnostic apparatuses 1, 1*a*, and 1*b* according to the first modification perform a process of correcting the sensitivity difference area D1. Consequently, the X-ray diagnostic apparatus 1, 1*a*, and 1*b* can suppress artifacts due to differences in the sensitivity of the X-ray detector 17.

Second Modification

The collection function 271, the filter processing functions 272 and 272*b*, the sensitivity difference area detection functions 273 and 273*b*, the signal estimation function 274, the correction information generation function 275, the correction function 276, the reconstruction function 277, the post-processing function 278, the inverse filter processing function 279, and the designated area setting function 280 may also be provided in other apparatuses as well as the X-ray diagnostic apparatuses 1, 1*a*, and 1*b*. For example, the above functions may be provided in a medical image processing apparatus implemented by a personal computer, a server, or a workstation. Moreover, the medical image processing apparatus may be implemented by a plurality of devices as well as one device.

More specifically, the medical image processing apparatus has an acquisition function of acquiring a plurality of projection data collected by the X-ray diagnostic apparatuses 1, 1*a*, and 1*b*. That is, the acquisition function acquires a plurality of projection data based on output signals from the X-ray detector 17 that rotates around the subject P.

The medical image processing apparatus has the filter processing functions 272 and 272*b*, the sensitivity difference area detection functions 273 and 273*b*, the signal estimation function 274, the correction information generation function 275, the correction function 276, the reconstruction function 277, the post-processing function 278, the inverse filter processing function 279, and the designated area setting function 280. Subsequently, the medical image processing apparatus performs various processes on the plurality of acquired projection data.

Third Modification

The X-ray diagnostic apparatuses 1, 1*a*, and 1*b* are described as executing the computer programs stored in the storage circuitry 21 to implement the collection function 271, the filter processing functions 272 and 272*b*, the sensitivity difference area detection functions 273 and 273*b*, the signal estimation function 274, the correction information generation function 275, the correction function 276, the reconstruction function 277, the post-processing function 278, the inverse filter processing function 279, and the designated area setting function 280. However, the X-ray diagnostic apparatuses 1, 1*a*, and 1*b* may implement, by hardware such as semiconductor circuitry, all or part of the collection function 271, the filter processing functions 272 and 272*b*, the sensitivity difference area detection functions 273 and 273*b*, the signal estimation function 274, the correction information generation function 275, the correction function 276, the reconstruction function 277, the post-processing function 278, the inverse filter processing function 279, and the designated area setting function 280. Moreover, these functions may also be implemented by a plurality of pieces of hardware as well as one piece of hardware.

According to at least one of the above-described embodiments and the like, artifacts due to differences in the sensitivity of the X-ray detector 17 can be suppressed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
    acquire a plurality of projection data based on an output signal from an X-ray detector that rotates around a subject,
    perform reconstruction filter processing on the plurality of acquired projection data, the reconstruction filter processing being included in reconstruction regarding the plurality of projection data,
    detect a sensitivity difference area formed in the plurality of projection data due to differences in sensitivity of the X-ray detector, on a basis of a processing result of the reconstruction filter processing,
    estimate a signal value when there are no differences in sensitivity in the sensitivity difference area,
    generate correction information on the sensitivity difference area on a basis of an estimation result, perform correction processing on the plurality of projection data on a basis of the correction information, and perform reconstruction processing including the reconstruction filter processing on the plurality of projection data subjected to the correction processing.

2. The medical image processing apparatus according to claim 1, wherein the processing circuitry stores the plurality of acquired projection data in storage circuitry, and performs the correction processing on the plurality of projection data stored in the storage circuitry, on the basis of the correction information.

3. The medical image processing apparatus according to claim 1, wherein the processing circuitry performs inverse filter processing on the processing results of the reconstruction filter processing by the reconstruction filter processing to return to a state before the reconstruction filter processing is performed, and performs the correction processing on a plurality of projection data generated by the inverse filter processing.

4. The medical image processing apparatus according to claim 1, wherein the processing circuitry acquires a plurality of projection data based on an output signal from the X-ray detector having different resolutions depending on a part of an area where an X-ray is detected.

5. The medical image processing apparatus according to claim 1, wherein the processing circuitry designates an area where the sensitivity difference area is searched, and performs the reconstruction filter processing on the designated area in the plurality of acquired projection data.

6. The medical image processing apparatus according to claim 1, wherein, on a basis of a signal value in an area other than the sensitivity difference area, the processing circuitry estimates a signal value when there are no differences in sensitivity in the sensitivity difference area.

7. The medical image processing apparatus according to claim 1, wherein the processing circuitry estimates that a signal value of a portion of the subject specified by a portion of the subject to which the sensitivity difference area belongs is the signal value when there are no differences in sensitivity in the sensitivity difference area.

8. An X-ray diagnostic apparatus comprising:

an X-ray detector configured to rotate around a subject; and processing circuitry configured to collect a plurality of projection data based on an output signal from an X-ray detector, perform reconstruction filter processing on the plurality of collected projection data, the reconstruction filter processing being included in reconstruction regarding the plurality of projection data, detect a sensitivity difference area formed in the plurality of projection data due to differences in sensitivity of the X-ray detector, on a basis of a processing result of the reconstruction filter processing, estimate a signal value when there are no differences in sensitivity in the sensitivity difference area, generate correction information on the sensitivity difference area on a basis of an estimation result, perform correction processing on the plurality of projection data on a basis of the correction information, and perform reconstruction processing including the reconstruction filter processing on the plurality of projection data subjected to the correction processing.

9. A medical image processing method comprising:

acquiring a plurality of projection data based on an output signal from an X-ray detector that rotates around a subject;

performing reconstruction filter processing on the plurality of acquired projection data, the reconstruction filter processing being included in reconstruction regarding the plurality of projection data;

detecting a sensitivity difference area formed in the plurality of projection data due to differences in sensitivity of the X-ray detector, on a basis of a processing result of the reconstruction filter processing;

estimating a signal value when there are no differences in sensitivity in the sensitivity difference area;

generating correction information on the sensitivity difference area on a basis of an estimation result;

performing correction processing on the plurality of projection data on a basis of the correction information; and performing reconstruction processing including the reconstruction filter processing on the plurality of projection data subjected to the correction processing.

10. A medical image processing apparatus comprising:

processing circuitry configured to acquire a plurality of projection data based on an output signal from an X-ray detector that rotates around a subject, perform reconstruction filter processing on the plurality of acquired projection data to emphasize a sensitivity difference area formed in the plurality of projection data, the reconstruction filter processing being included in reconstruction regarding the plurality of projection data, the sensitivity difference area indicating a difference in sensitivity between a plurality of detection elements of the X-ray detector, generate correction information on the sensitivity difference area on a basis of a processing result of the reconstruction filter processing, perform correction processing on the plurality of projection data on a basis of the correction information, and perform reconstruction processing including the reconstruction filter processing on the plurality of projection data subjected to the correction processing.

* * * * *